United States Patent [19]
Kautzer et al.

[11] Patent Number: 5,528,264
[45] Date of Patent: Jun. 18, 1996

[54] WIRELESS REMOTE CONTROL FOR ELECTRONIC EQUIPMENT

[75] Inventors: Jeffrey A. Kautzer, Waukesha; Timothy P. Putra, Wales; Gary F. Relihan, Nashotah, all of Wis.

[73] Assignee: General Electric Company, Milwaukee, Wis.

[21] Appl. No.: 118,409

[22] Filed: Sep. 8, 1993

Related U.S. Application Data

[63] Continuation of Ser. No. 813,228, Dec. 23, 1991, abandoned.

[51] Int. Cl.⁶ .................................................... G09G 5/00
[52] U.S. Cl. .............................................. 345/158; 348/734
[58] Field of Search ............................... 340/706, 709, 340/710, 711, 825.69, 825.72; 341/176, 177; 358/194.1, 210; 375/8, 121, 22, 272, 303; 345/156, 157, 158; 455/352, 353; 359/147, 189; 348/734

[56] References Cited

U.S. PATENT DOCUMENTS

| | | | |
|---|---|---|---|
| 4,209,255 | 6/1980 | Heynau et al. | 340/709 |
| 4,245,347 | 1/1981 | Hutton et al. | 455/352 |
| 4,481,678 | 11/1984 | Sakamoto et al. | 359/189 |
| 4,565,999 | 1/1986 | King et al. | 340/709 |
| 4,654,648 | 3/1987 | Herrington et al. | 340/710 |
| 4,745,402 | 5/1988 | Auerbach | 340/709 |
| 4,787,051 | 11/1988 | Olson | 340/710 |
| 4,854,691 | 8/1989 | Herr | 375/22 |
| 4,862,152 | 8/1989 | Milner | 340/712 |
| 4,878,055 | 10/1989 | Kasahara | 340/825.72 |
| 4,885,433 | 12/1989 | Schier | 178/19 |
| 4,959,721 | 9/1990 | Micic et al. | 340/709 |
| 5,020,154 | 5/1991 | Zierhut | 455/102 |
| 5,142,398 | 8/1992 | Heep | 358/194.1 |
| 5,146,210 | 9/1992 | Herberle | 340/709 |

FOREIGN PATENT DOCUMENTS

| | | | |
|---|---|---|---|
| 0211727 | 2/1987 | European Pat. Off. | G06K 11/06 |
| 0211984 | 3/1987 | European Pat. Off. | G06K 11/06 |
| 3838605 | 5/1990 | Germany | G06F 3/03 |
| 58-170741 | 9/1983 | Japan . | |
| 59-123239 | 6/1984 | Japan . | |
| 60-46539 | 3/1985 | Japan . | |
| 63-187716 | 1/1989 | Japan . | |

*Primary Examiner*—Richard Hjerpe
*Assistant Examiner*—Kara Farnandez Stoll
*Attorney, Agent, or Firm*—Quarles & Brady

[57] ABSTRACT

A hand-held device produces an omnidirectional beam of infra-red light which can be aimed by the user. A plurality of detectors positioned in a rectangular array adjacent a video monitor and each detector produces an electrical signal that varies as a function of the light intensity impinging thereon. A circuit compares the signals from the detectors to determine coordinates of a position on the monitor at which to place a cursor. A linear transfer function is applied to the detector signals before determining the coordinates. The coordinates are processed by a seventh order recursive digital filter and the resultant position must be a minimum distance from the present position before the cursor is relocated. By varying the direction of the light beam the cursor position can be changed. When the cursor is at the position desired by the user, the hand-held device is activated to produce a different light beam. The circuit responds to this change in the light beam by producing a signal indicating that the user has selected the present position of the cursor.

10 Claims, 3 Drawing Sheets

WIRELESS REMOTE CONTROL FOR ELECTRONIC EQUIPMENT

This application is a continuation of application Ser. No. 07/813,228, filed Dec. 23, 1991, now abandoned.

BACKGROUND OF THE INVENTION

The present invention relates to wireless remote controls; and specifically to such controls for operating medical imaging equipment like the one described in U.S. Pat. No. 4,930,145.

Many types of electronic equipment employ wireless remote controls which allow the user to operate the equipment from a distance. Televisions, video cassette recorders, and other consumer electronic products commonly use such controls. Conventional remote controls are hand-held units with a plurality of buttons corresponding to different functions of the equipment being controlled. When the user presses one of the buttons, a switch is closed which causes the control to generate a beam of infrared light. The light beam is modulated with digital information indicating the specific button that was activated by the user and thereby the function which has been selected. An infrared detector on the controlled equipment senses the beam of light and produces an electrical signal containing the digital information carried by that beam. The digital signal is decoded to determine the function to be performed by the equipment. Such wireless remote controls allow the user to operate the electronic equipment by selecting a variety of functions from a remote position free from cabling and other physical constraints.

Similar remote controls have been used with medical imaging systems, such as fluoroscopic cardiac equipment. In these imaging systems, the patient is positioned between an X-ray emitter and a detector to produce an image of the desired portion of the patient's anatomy. In fluoroscopic systems, a camera is used to produce a video signal from the X-ray image which is displayed on a monitor adjacent the patient. A physician stands near the patient and within several feet of the monitor. It is not uncommon for the physician to move about the patient during a fluoroscopic examination. In order to permit the physician to be at a number of positions and still control the apparatus, wireless remote controls similar to those used with consumer electronic equipment have been provided to control the X-ray system.

The physician often manipulates the patient or a medical implement inserted in the patient during the fluoroscopic examination. Thus, at least one hand of the physician must be free to perform the manipulation. This created problems with respect to the use of conventional remote controls that were difficult to operate with one hand due to the large number of buttons. Furthermore, some remote controls require several buttons to be pressed in sequence to activate certain functions.

As electronic equipment and medical imaging systems have become more complex, the number of functions which an operator would like to control from a remote location has increased. Thus, a need exists for a wireless remote control which can conveniently be utilized to operate a large number of functions with a single hand.

Many medical imaging systems are able to calculate the relative size of anatomical features in the video image. To do so, the physician identifies the boundary of the feature using a cursor and pressing a button when the cursor is properly positioned. Therefore, it also is desirable to provide an easy to use remote control for positioning a cursor to demarcate anatomical features in the image.

SUMMARY OF THE INVENTION

The present invention is useful to control the position of a cursor on a display monitor by producing a beam of radiation in a substantially omnidirectional pattern over a predetermined conical angular segment. The apparatus is wireless and operable by the user to vary the direction of the beam. The beam is received by one or more of a plurality of detectors positioned in a two dimensional array, which preferably is adjacent the monitor. Each detector produces an electrical signal having a characteristic that varies as a function of the intensity of the radiation impinging the detector. By comparing this characteristic of the electrical signals from the detectors, the position in which the operator desires the cursor to move can be approximated.

In one embodiment, the invention controls a medical imaging system and more specifically the cursor movement on an image display monitor. A single button is used to provide easy single-handed remote control operation, although additional buttons may be provided. With single button operation, when the remote control is aimed at the display station and the button is held depressed, the cursor is moved on the screen as indicated by the operator. When the cursor is in the desired position, the operator releases the button on the remote control, thereby indicating the desired function on the display screen which corresponds to that cursor position.

The display monitor in the medical imager embodiment serves two major purposes. One is the display of image information from the medical examination and the other is the presentation of control menus to the operator. The present invention also includes a means to drive a menu selection process whereby items are selected by positioning the cursor on the display station and upon release of the enable button on the remote control, the function selection is made. The function menus may include imaging processing functions, patient information, entry and display and interfacing functions with peripheral systems, such as remote viewing sights and printers.

An object of the present invention is to enable a user to remotely control electronic equipment without being tied to one location at which the controls are located.

Another object is to provide a remote control which can be operated anywhere in a three-dimensional region without having to be placed on a surface.

DESCRIPTION OF THE PRESENT INVENTION

Figure 1:
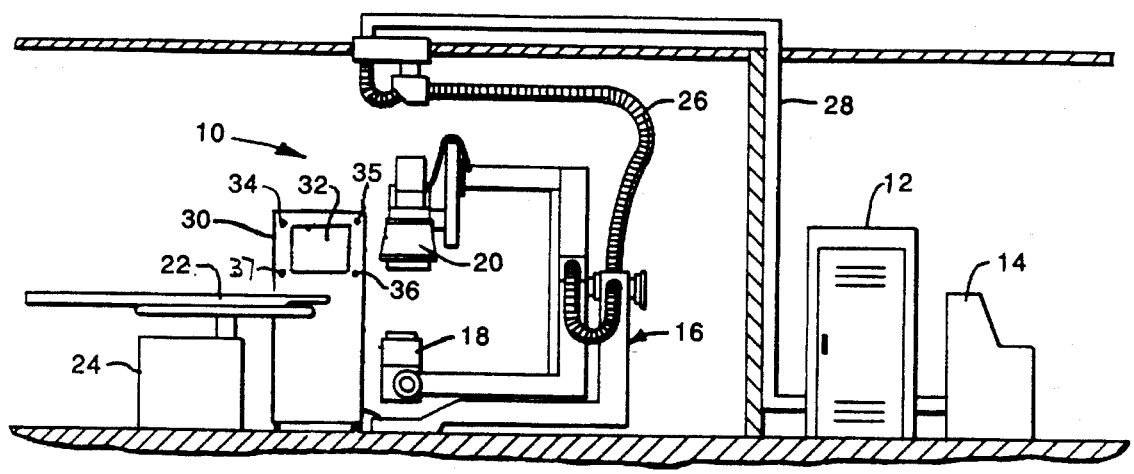
FIG. 1 is a pictorial representation of a medical imaging system incorporating the present invention.

Referring initially to FIG. 1, a medical imaging system 10 is installed in two rooms of a building, such as a hospital or medical clinic. Within one room is a power supply 12 and an operator console 14 containing control circuits. In the other room is a gantry arrangement 16 on which the X-ray tube assembly 18 and X-ray detection assembly 20 are mounted. The X-ray detection assembly 20 consists of a film holder and a video camera, or in the case in computed tomography, an X-ray detector which converts X-ray intensity into electrical signals. Electrical cables, that transfer power and control signals, extend through the flexible conduit 26 and rigid conduit 28 from the components mounted on the gantry 16 to the power supply 12 and control console 14.

An X-ray transmissive table 22 for supporting a patient being examined, is positioned adjacent to the gantry 16. The table 22 is mounted on support 24 in a manner that allows the table to slide between the X-ray tube assembly 18 and the X-ray detection assembly 20.

A display console 30 is located adjacent the patient table 22 and includes video monitor 32 on which a physician can view the X-ray image from the video camera within the detection assembly 20. The monitor 32 can be a cathode ray tube device, a liquid crystal display or another type of display device. A separate infrared light detector 34, 35, 36 and 37 is mounted adjacent each of the four corners of the monitor 32 in a square as the image display of the monitor screen also is square. However, the detectors can be arranged in a rectangle to correspond to a rectangular image. The display console 30 is mounted on casters which allow it to be positioned at different locations with respect to the table 22. A multiple conductor signal cable connects the display console to the circuits in the operator console 14.

Although images of a patient lying on table 22 can be produced when an X-ray technician is at console 14, many examination procedures require the technician or a physician to stand adjacent the table. That person also may stand adjacent to the table during the initial configuration of the system for an exposure and then leave the room during the actual exposure. At such times, when the technician or physician is adjacent to the table, that person can control the system 10 utilizing a hand-held remote control unit which sends infrared light signals to the detectors 34–37 on the display console 30. Although infrared light beams preferably are used as the communication medium between the remote control unit and the display console 30, other wavelengths of radiation, such as ultrasound, may be used. Regardless of which wavelength is used, it must be transmitted in a relatively omnidirectional beam which can be aimed selectively at different detectors. 34–37.

Figure 2:
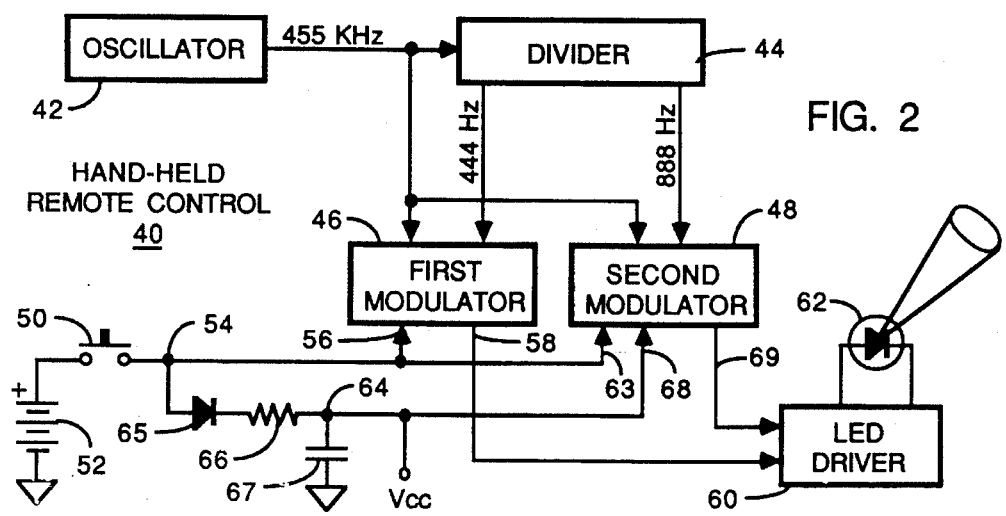
FIG. 2 is a schematic block diagram of a hand-held remote control for the imaging system.

As shown in FIG. 2, a hand-held remote control 40 has an oscillator 42 that generates an alternating electrical signal having a frequency of about 455 kilohertz, for example. The signal from oscillator 42 is applied to the input of a frequency divider 44 which produces two output signals at 444 Hertz and 888 Hertz. The output of the oscillator 42 is applied to both a first and a second modulator 46 and 48, respectively. The first modulator 46 also receives the 444 Hertz signal from the divider 44 and the second modulator 48 receives the other output signal from the divider.

The remote control 40 is operated by a single pushbutton switch 50 which selectively couples the positive terminal of a battery 52 to a first node 54. The first modulator 46 is enabled by positive voltage from the first node 54 being applied to an input terminal 56. When this occurs, the first modulator 46 produces a pulsed output signal on line 58. This output signal consists of pulses of the 455 kilohertz oscillator signal which occur at a frequency of 444 Hertz. Line 58 is connected to the input of a light emitting diode (LED) driver 60. The LED driver 60 applies the pulsed signal to an infrared light emitting diode 62 which generates a beam of infrared light that is modulated by the pulsed signal from component 46. The light beam is emitted in substantially an omnidirectional pattern over a predefined conical angular segment. This allows the beam selectively to be directed toward one or more of the detectors 34–37 on the display console 30. The intensity level of the light at a given distance from the light emitting diode 62 decreases as a function of the transverse distance from a center of the beam.

The first node 54 also is connected to the enable terminal 63 of the second modulator 48, which is disabled whenever a positive voltage is applied to that terminal. When the second modulator 48 is enabled, an output signal is produced on line 69 consisting of pulses of the 455 kilohertz oscillator signal occurring at a frequency of 888 Hertz. This higher frequency pulsed signal is applied to LED driver 60 to modulate the light beam from LED 62.

The pulsed output signals from the first and second modulators 46 and 48 have a twenty to twenty-five percent duty cycle, for example. However, the power consumption of the remote control 40 can be reduced by decreasing the duty cycle of both the output signals to a smaller percent.

The first node 54 is coupled to a second node 64 by a diode 65 and resistor 66 connected in series between those nodes. The diode 65 is connected so that current flows from node 54 to node 64. The second node 64 is coupled to the circuit ground by a storage capacitor 67. The voltage at the second node 64 supplies power to the second modulator 48 via terminal 68. Voltage (Vcc) at the second node 64 is also the source of power for the oscillator 42 and divider 44.

To operate the remote control 40, the user aims it toward the display console 30 and closes pushbutton switch 50 to supply power from battery 52 to the components of the control. When power is initially applied, the oscillator 42 begins generating the 455 kilohertz signal from which the divider 44 produces the two lower frequency output signals. The positive voltage from the battery 52 is applied to the input terminal 56 of the first modulator which responds by generating a burst of the 455 kilohertz signal every 2.25 milliseconds. This output signal from the first modulator 46 is applied to the LED driver 60 and the infrared LED 62, thereby producing an infrared light beam which is pulsed by the signal from the first modulator 46.

The remote control 40 can be used to position cursor in an image being displayed on the monitor 32. For example the cursor can select an item on a menu being displayed along with the X-ray image or by itself on monitor 32. Alternatively, separate monitors can be provided in the display console 30 for the X-ray image and control means. As will be described, the user controls the position of a cursor on the screen of the monitor 32 by aiming the activated hand-held remote control 40 at the general location on the screen where the cursor is to be positioned. The cursor will move to a new position in response to the intensity of the infrared light which strikes each of the detectors 34–37. Depending on the ability of the user to accurately point the remote control 40, several aiming interations may be required to move the cursor to the desired position.

When the user has positioned the cursor over the desired menu item, the pushbutton switch 50 is released, opening the switch and terminating the application of a positive voltage from battery 52 to node 54. This termination of the positive voltage causes the first modulator 46 to cease operation, as power has been removed from terminal 56. However, the voltage stored across capacitor 67 is sufficient to continue energizing oscillator 42, divider 44 and second modulator 48. When the voltage applied from node 54 to terminal 63 of the second modulator 48 is no longer positive, the second modulator will be enabled as long as the positive voltage still is applied to its power supply terminal 68 from node 64. At this time, the second modulator begins producing a burst of the 455 kilohertz signal every 1.126 milliseconds. This signal is transmitted via line 69 to the LED driver 60 thereby generating an infrared light beam from LED 62 that is pulsed by that signal. For a period of time until capacitor 67 discharges, the output from the hand-held remote control 40 changes to reoccurring bursts of the oscillator signal at a rate of 888 Hertz. This change in burst rate from 444 Hertz to 888 Hertz is detected by circuitry in the display console 30 which produces a signal indicating that the user has selected the menu item at the present position of the cursor being displayed on monitor 32. Alternatively, a character could be transmitted digitally to indicate the selection of the menu item at which the cursor is positioned. As similar cursor movement procedure can be employed to mark reference points on an X-ray image, such as for sizing a stenosis in a blood vessel.

Figure 3:
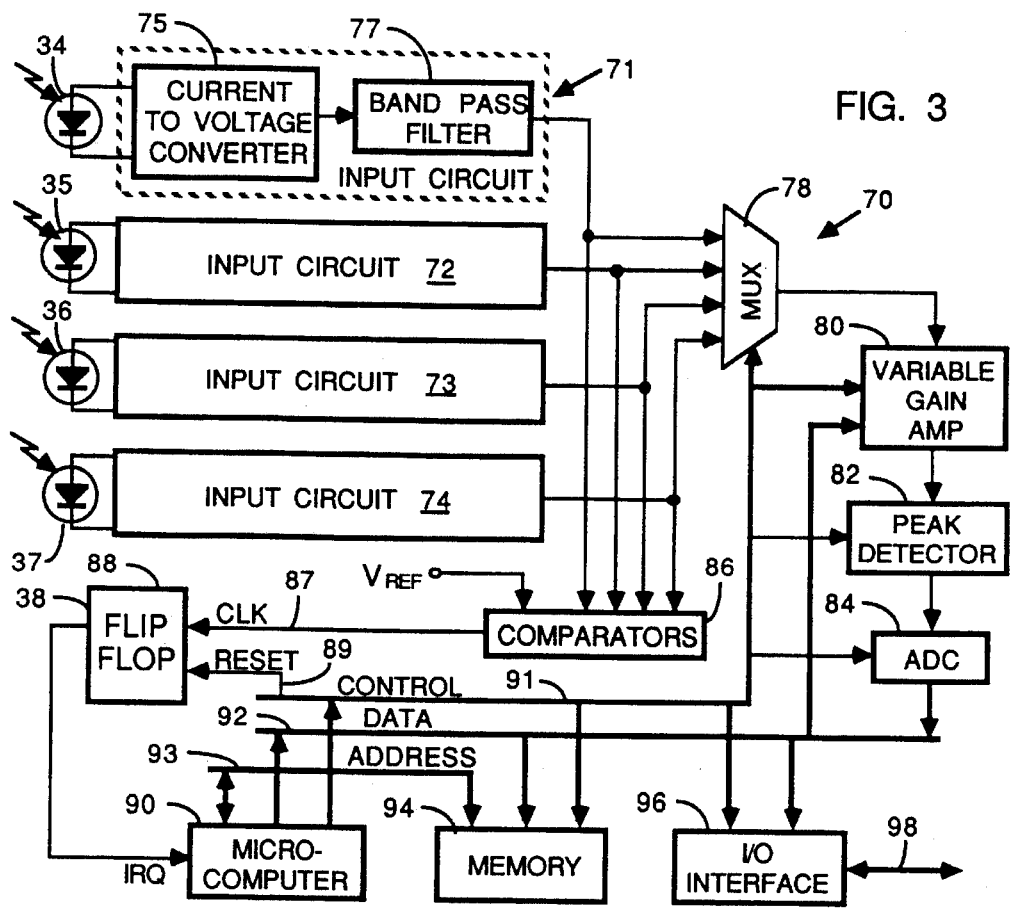
FIG. 3 is a schematic block diagram of a circuit with receives a signal from the remote control.

FIG. 3 shows the circuitry of a receiver 70 in the display console 30 which detects the infrared light from the hand-held remote control 40 and calculates where to move the cursor. The four infrared light detectors 34–37 are connected to separate input circuits 71–74, respectively. In each input circuit, the associated detector is connected to a current to voltage converter 75 to produce an output signal having a voltage which is proportional to the intensity of the light striking the detector. This output signal is applied to a band pass filter 77 that has a center frequency equal to the frequency of oscillator 42 in the remote control 40. The band pass filter 77 removes extraneous signals due to infrared radiation at other frequencies than those emitted by the remote control.

The outputs of the band pass filters 77 in each input circuit 71–74 are connected to inputs of a four-to-one analog multiplexer 78. The multiplexer. 78 responds to a control signal by coupling one of its inputs to the input of a variable gain amplifier 80. The output of the variable gain amplifier 80 is applied to a peak detector 82. As will be described, the peak detector 82 is reset each time a new multiplexer input is selected to produce an output voltage that corresponds to the peak intensity of the light sensed by the corresponding detector 34–37. This output voltage is digitized by an analog to digital converter (ADC) 84.

The outputs of the four input circuits 71–74 also are connected to a set of voltage comparators 86. Each input circuit output is compared to a reference voltage $V_{REF}$ which is exceeded when infrared light from the remote control 40 is striking the associated detector 34–37. The results of the comparisons are logically ANDed to produce a signal on line 87 whenever any one of the detectors senses light from the remote control 40. Line 87 is connected to the clock (CLK) input of flip-flop 88, the output of which is coupled to an interrupt request input (IRQ) of a microcomputer 90. The flip-flop 88 is reset by signal on control line 89.

The microcomputer 90 can be any one of several commercially available models which include internal counters, timers and random access memory. The microcomputer 90 is connected to a group of control lines forming bus 91, to a parallel data bus 92 and to a parallel address bus 93. The control and data buses 91 and 92 carry signals between the microcomputer 90 and the multiplexer 78, variable gain amplifier 80, peak detector 82 and ADC 84.

Also connected to the buses 91–93 is a memory 94 which stores a program that is executed by the microcomputer 90, as will be described. A I/O interface circuit 96, such as a universal asynchronous receiver/transmitter, is connected to the control and data buses 91 and 92 for the exchange of data over a communication link 98 with the circuits in the operator console 14 that control the monitor display.

Figure 4B:
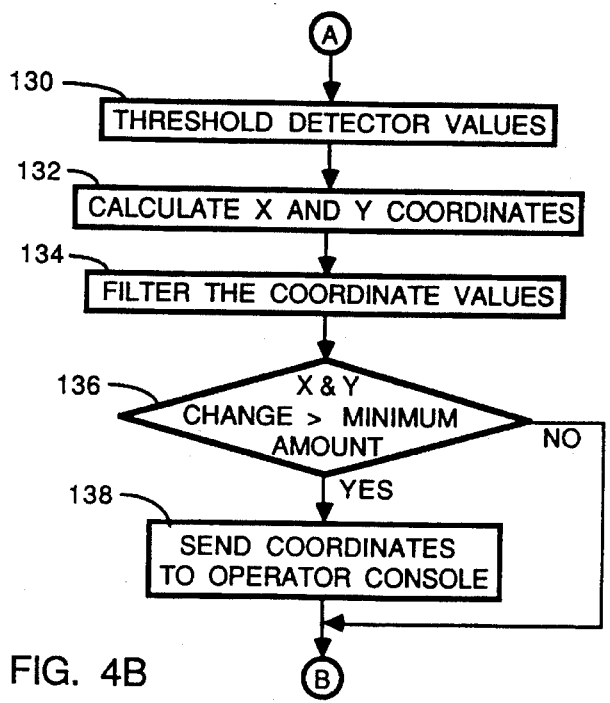
FIGS. 4A and 4B are a flow-chart of a program executed by the circuit in FIG. 3.
Figure 4A:
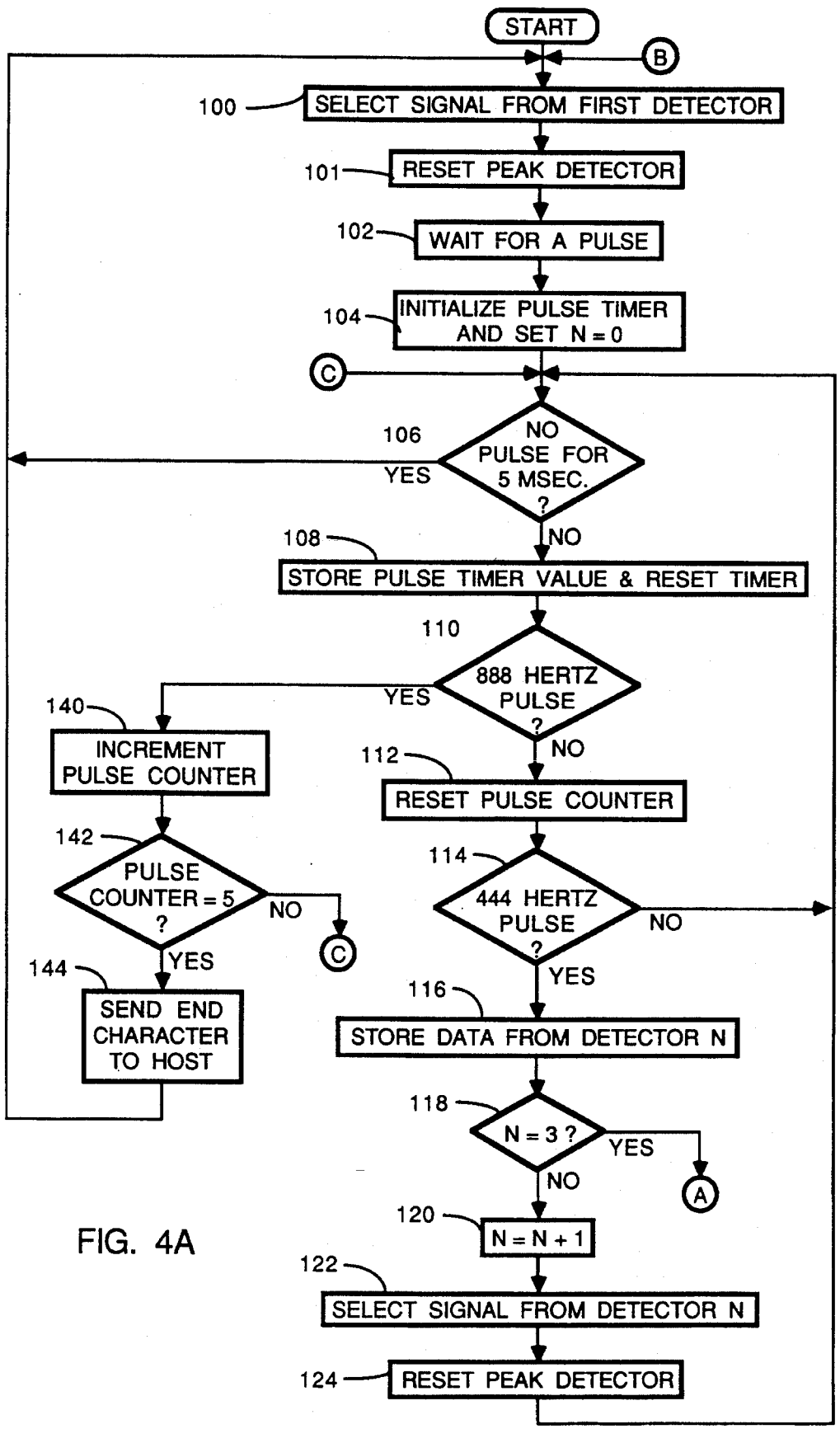

With reference to FIG. 4, the microcomputer 90 executes a program that commences at step 100. At that point, the microcomputer issues a signal via control bus 91 which causes the multiplexer 78 to couple the output from the first input circuit 71 to the variable gain amplifier 80. A signal is sent by microcomputer 90 which resets the peak detector 82 at step 101. Then the microcomputer enters a dormant state at step 102 waiting for an interrupt request from flip-flop 88. When any one of the four detectors 34–37 senses infrared light produced by the remote control 40, the input circuit 71–74 produces an output signal that causes the associated comparator in set 86 to toggle the flip-flop 88. The toggling of flip-flop 88 produces an active interrupt request to the microcomputer indicating that a pulse of infrared light from the remote control has been received. When such a pulse is discovered at step 102, the microcomputer issues a signal over line 89 of control bus 91 to reset the flip-flop 88 terminating the interrupt request. Next, a light detector indicator variable N is set to zero to indicate the first detector has been selected. Then a timer which measures the interval between the beginning of consecutive pulses from the remote control is initialized to zero at step 104.

The program execution then advances to step 106 where the microcomputer 90 waits for another interrupt request which indicates that a second infrared light pulse has been received from the remote control 40. If a second light pulse is not received within five milliseconds from the first pulse as indicated by the pulse timer, the program execution returns to step 100 without determining a new cursor position. As noted previously, the lowest frequency at which pulses are emitted by the remote control produces a pulse every 2.252 milliseconds. Thus, if a second pulse does not occur for five milliseconds, a determination is reached by the computer program that the previous interrupt was erroneous.

When a second pulse occurs within the five millisecond time period at step 106, the program execution advances to step 108 where the value of the pulse timer is stored in the microcomputer's internal memory and the timer is then reset to measure the interval which elapses until the next pulse is received. At step 110, the stored value from the pulse timer is evaluated to determine if the pulses are occurring at the 888 Hertz frequency, in which case the timer value will be equivalent to approximately 1.126 milliseconds. The initial group of pulses from the remote control will not be at this higher frequency, as they occur while the user is depressing pushbutton 50. Therefore, the program execution initially will advance to step 112 at which a counter of the 888 Hertz pulses is reset.

The previously stored value from the pulse timer is examined at step 114 to determine if the pulses are occurring at the 444 Hertz rate. When these lower frequency pulses are being received, the timer value Will be approximately equal to 2.252 milliseconds. If this is not the case, the program execution returns to step 106 as a valid pulse was not received. When the pulses are occurring at the lower frequency rate, step 116 is executed to store the data indicating the intensity of light received by one of the detectors 34–37.

At step 118, a determination is made whether the detector indicator variable N is equal to three which occurs when intensity data from all of the detectors 34–37 have been stored in the microcomputer's memory. If such have not occurred, the detector indicator variable N is incremented at step 120. Next, the microcomputer 90 sends a control signal to multiplexer 78 at step 122 to couple the output signal from the first input circuit for the next detector to the variable gain amplifier 80. The peak detector is reset at step 124. Thereafter, the program execution returns to step 106 to await another light pulse from the remote control which is used to measure the intensity of the light sensed by another one of the detectors 35-37.

Eventually, the program loops through steps 106-124 four times, thereby accumulating data from each of the sensors 34-37. When this occurs, the execution branches from step 118 to a portion of the program beginning at step 130 that uses the light intensities to calculate where the cursor is to be repositioned.

When the remote control 40 is being aimed the detectors (e.g. 35 and 36) on one side of the monitor 32, light from the LED 62 still may strike the detectors (e.g. 34 and 37) on the other side of the monitor, depending upon the distance between the user of the remote control and the display console 30. The same is true with respect to aiming the remote control at the upper or lower pairs of detectors to move the cursor vertically. Thus when the user desires to move the cursor to one edge of the screen of the monitor, some amount of light may be sensed by the detectors along the opposite edge. As a consequence, a simple comparison Of the magnitudes of the raw light intensities would not indicate that the cursor should move to the extreme edge of the screen in this case.

To overcome this problem, a linear transfer function is applied to the four the light intensity values at step 130. If a light intensity value is less than a defined threshold, the value is transformed to zero, otherwise the threshold is subtracted from the light intensity value to obtain a transformed value. The transformed set of four intensity values are stored in memory 94. The value of the threshold can be determined empirically during configuration of the X-ray system 10. To do so a technician stands at a fixed operating distance from the monitor 32 and aims the remote control 40 directly at the detectors along one edge of the screen. The light intensity sensed by a detector at the opposite edge of the screen is used to set the threshold.

At step 132, the microcomputer 90 uses the four transformed intensity values to calculate a new position for the cursor on the monitor screen. This position is denoted by a pair of coordinates X and Y which indicate the distance along horizontal and vertical axes of the screen at which to position the cursor. These coordinates are calculated according to one of the following sets of equations:

$$X = \left( \frac{V2 + V3}{V1 + V2 + V3 + V4} \right) W \text{ and}$$

$$Y = \left( \frac{V1 + V2}{V1 + V2 + V3 + V4} \right) H \text{ or}$$

$$X = \left( \frac{V1 + V4}{V1 + V2 + V3 + V4} \right) W \text{ and}$$

$$Y = \left( \frac{V3 + V4}{V1 + V2 + V3 + V4} \right) H$$

where V1, V2, V3 and V4 are the digitized peak voltages of the signals from the first, second, third and fourth light detectors 34, 35, 36 and 37, respectively. W and H represent the number of positions for the cursor on the monitor screen in the horizontal and vertical dimensions, respectively. For example, 256, 512 or 1024 unique positions may be defined in each dimension.

The calculated values for the X and Y coordinates are passed through a seventh order recursive digital filter to remove the effects of high frequency electronic noise from affecting the cursor positioning at step 134. The equations of the filter are:

$$Xf(n) = k0*X(n) + k1*X(n-1) + \ldots + k7*X(n-7)$$

$$Yf(n) = k0*Y(n) + k1*Y(n-1) + \ldots + k7*Y(n-7)$$

The typical user can not hold the remote control 40 perfectly still and even slight movement of the control can produce a jittery cursor on the monitor screen. To eliminate such jitter, the filtered values of the X and Y coordinates are compared at step 136 to the coordinates for the present position of the cursor which were stored during a previous pass through the program. If neither coordinate has changed by a defined minimum amount, for example by at least four positions when 1024 positions are defined in that direction on the screen, the program assumes that the change was due a trembling operator hand. In this case the new coordinate values are ignored, the cursor position is unchanged and the program execution branches to step 100 to repeat the process.

If a significant change in the coordinates is detected at step 136, the filtered coordinates are sent at step 138 through the I/O interface 96 and communication link 89 to the circuitry in the operator console 14 which controls the cursor position. Such circuitry is well known in the computer field and can be similar to that described in U.S. Pat. No. 4,259,725. The program execution then returns to step 100 to await another pulse of light from the remote control 40.

Eventually the user releases the pushbutton 50 to indicate that the cursor has been positioned over the desired item in the monitor image. The release of the pushbutton 50 causes the remote control to generate a series of light pulses at the 888 Hertz rate, as previously described. This change in frequency is detected at step 110 and the program execution branches to step 140 where a pulse counter is incremented. This pulse counter is then checked at step 142 to determine whether five consecutive pulses at this higher frequency have been received. If not, the program execution returns to step 106 to wait for another pulse of light from the remote control 40. When five consecutive pulses at the 888 Hertz rate have been received, the microcomputer 90 sends a unique data character to the control circuitry within the operator console 14 to indicate that the user has selected the point on the monitor screen at which the cursor is currently being positioned at step 136. The control circuitry can use the cursor position in a conventional manner to determine the menu option that was selected. The program execution by the receiver 70 returns to step 102 to wait for the user to once again activate the remote control 40.

The invention being claimed is:

1. A remote control for use with an apparatus for positioning a cursor on a monitor screen in which the apparatus includes a plurality of radiation detectors and a mechanism that determines a position at which to place the cursor by comparing signals from the detectors; said remote control comprising:

a user operable switch having first and second states;

a signal generator that produces an alternating signal which alternates at a given frequency;

a first means for producing a first signal formed by pulses of the alternating signal which pulses of the first signal occur at a first rate;

a second means for producing a second signal formed by pulses of the alternating signal which pulses of the second signal occur at a second rate; and a radiation emitter connected to said first and second means for producing signals, said emitter producing a beam of radiation which is modulated by the first signal in response to said switch being in the first state, and producing a beam of radiation which is modulated by the second signal in response to said switch being in the second state.

2. The system as recited in claim 1 further comprising a time determining means which causes said emitter to produce a beam of radiation which is pulsed by the second signal only for a defined interval of time while said switch is in the second state, so that after the defined interval of time said emitter does not produce a beam of radiation until said switch is placed into the first state.

3. The system as recited in claim 1 wherein said signal generator comprises:

an oscillator that generates the alternating signal; and a frequency divider that produces a first control signal that alternates at the first rate and a second control signal that alternates at the second rate;

wherein the alternating signal and the first control signal are applied to the first means for producing, and the alternating signal and the second control signal are applied to the second means for producing.

4. An apparatus to input information into a programmable device, said apparatus comprising:

a hand-held control including:

(a) a signal generator that generates an alternating signal having a given frequency, and produces a first signal formed by pulses of the alternating signal which pulses of the first signal occur at a first rate and produces a second signal formed by pulses of the alternating signal which pulses of the second signal occur at a second rate, (b) a user operable switch coupled to the signal generator, (c) a timer which defines a period of time and which is coupled to the signal generator, and (d) a light emitter being driven by the first signal to emit light when the switch is in a first state, and being driven by the second signal to emit light for only the period of time defined by said timer when the switch is in the second state wherein after that period of time said emitter does not emit light until said switch is placed into the first state;

means for displaying information;

means for generating indicia of operational parameters of the programmable device on said means for displaying information;

a plurality of detectors responsive to light from said light emitter and located in a two-dimension array in proximity to said means for displaying information, each detector producing an electrical signal having a characteristic that varies as a function of an intensity of light impinging thereupon;

a positioning means, responsive to the electrical signals from said plurality of detectors, for determining a position at which to locate a cursor on said means for displaying information;

means, responsive to said positioning means, for generating a cursor on said means for displaying information; and means for determining a selection of an indicia by a user in response to a signal from said detectors and the location of the cursor received from said positioning means.

5. The apparatus as recited in claim 4 wherein said positioning means comprises:

means for calculating X and Y coordinates which indicate the position at which to place the cursor; and a low pass filter connected to said means for calculating for removing effects of electronic noise from the X and Y coordinates.

6. The apparatus as recited in claim 5 wherein said positioning means determines a position at which to locate the cursor only when that position differs by at least a given amount from a present position of the cursor.

7. The apparatus as recited in claim 4 wherein:

said positioning means determines a position at which to locate a cursor in response to said plurality of detectors sensing pulses of light occurring at the first rate; and said means for determining a selection of an indicia being responsive to said plurality of detectors sensing pulses of light occurring at the second rate.

8. The system as recited in claim 4 wherein:

said plurality of detectors are positioned at edges of a rectangle adjacent said means for displaying information; and said means for determining a position calculates X and Y coordinates indicating the position at which to place the cursor according to the following equations:

$$X = \left( \frac{Vb + Vc}{Va + Vb + Vc + Vd} \right) W$$

$$Y = \left( \frac{Va + Vb}{Va + Vb + Vc + Vd} \right) H$$

where Va, Vb, Vc and Vd represent a characteristic of the signal from a different detector, W represents a maximum value for the X coordinate, and H represents a maximum value for the Y coordinate.

9. The system as recited in claim 4 wherein said positioning means applies a linear transfer function to values representing the characteristics of the electrical signals before determining a position on said means for displaying information at which to place the cursor.

10. The system recited in claim 9 wherein the application of the linear transfer function converts characteristic values below a defined threshold to zero.

* * * * *